(12) United States Patent
Kang et al.

(10) Patent No.: US 9,949,710 B2
(45) Date of Patent: Apr. 24, 2018

(54) X-RAY IMAGING APPARATUS AND CONTROL METHOD FOR THE SAME

(71) Applicant: Samsung Electronics Co., Ltd., Gyeonggi-do (KR)

(72) Inventors: Dong Goo Kang, Gyeonggi-do (KR); Young Hun Sung, Gyeonggi-do (KR); Seok Min Han, Gyeonggi-do (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 180 days.

(21) Appl. No.: 15/026,959

(22) PCT Filed: Oct. 1, 2014

(86) PCT No.: PCT/KR2014/009268
§ 371 (c)(1),
(2) Date: Apr. 1, 2016

(87) PCT Pub. No.: WO2015/050377
PCT Pub. Date: Apr. 9, 2015

(65) Prior Publication Data
US 2016/0296194 A1  Oct. 13, 2016

(30) Foreign Application Priority Data
Oct. 1, 2013  (KR) .......................... 10-2013-0117178

(51) Int. Cl.
*G06T 11/00* (2006.01)
*A61B 6/00* (2006.01)

(52) U.S. Cl.
CPC ................ *A61B 6/54* (2013.01); *A61B 6/405* (2013.01); *A61B 6/4035* (2013.01);
(Continued)

(58) Field of Classification Search
CPC ......... A61B 6/487; A61B 6/481; A61B 6/504; A61B 6/4028; A61B 6/488; A61B 6/503
(Continued)

(56) References Cited

U.S. PATENT DOCUMENTS

| 8,891,843 B2 | 11/2014 | Ohishi |
| 9,025,840 B2 | 5/2015 | Waechter-Stehle et al. |
| 2011/0293164 A1* | 12/2011 | Sato ..................... A61B 6/5264 382/132 |

FOREIGN PATENT DOCUMENTS

| JP | 2011-019573 A | 2/2011 |
| JP | 2012-061307 A | 3/2012 |

(Continued)

OTHER PUBLICATIONS

International Search Report dated Jan. 12, 2015 in connection with International Application No. PCT/KR2014/009268; 3 pages.

(Continued)

*Primary Examiner* — Don Wong

(57) ABSTRACT

Disclosed herein are an X-ray imaging apparatus and a control method for the same. The control method for the X-ray imaging apparatus includes acquiring a mask image by irradiating an object with X-rays, determining a movement of the object based on the mask image, generating a plurality of X-ray images of mutually different energy bands when the movement of the object is detected, and generating a single X-ray image of a single energy band when the movement of the object is not detected, and acquiring a blood vessel X-ray image based on the generated X-ray image.

22 Claims, 10 Drawing Sheets

(52) U.S. Cl.
   CPC ............ *A61B 6/4464* (2013.01); *A61B 6/461* (2013.01); *A61B 6/467* (2013.01); *A61B 6/481* (2013.01); *A61B 6/482* (2013.01); *A61B 6/504* (2013.01); *A61B 6/5235* (2013.01)

(58) Field of Classification Search
   USPC .......................................................... 378/42
   See application file for complete search history.

(56) References Cited

FOREIGN PATENT DOCUMENTS

| | | |
|---|---|---|
| KR | 10-2006-0065497 A | 6/2006 |
| KR | 10-2010-0120595 A | 11/2010 |
| WO | WO 2011/110987 A1 | 9/2011 |

OTHER PUBLICATIONS

Written Opinon of the International Searching Authority dated Jan. 12, 2015 in connection with International Application No. PCT/KR2014/009268; 4 pages.

\* cited by examiner

[Fig. 1]
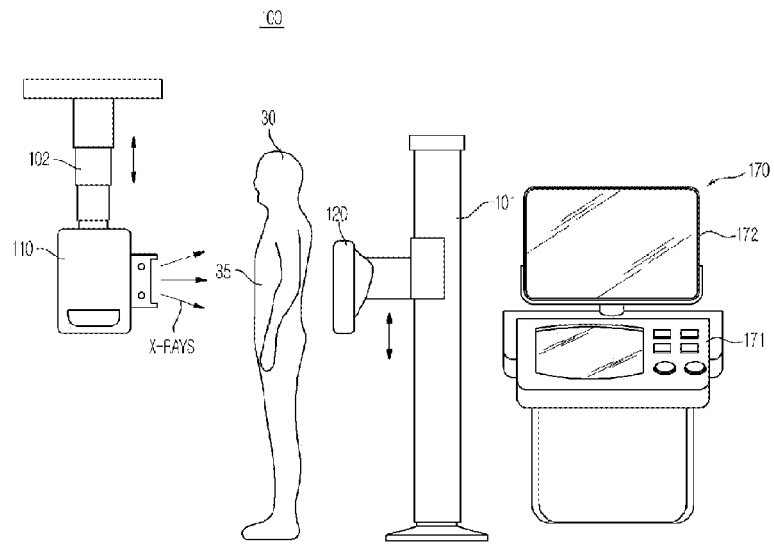
[Fig. 2]
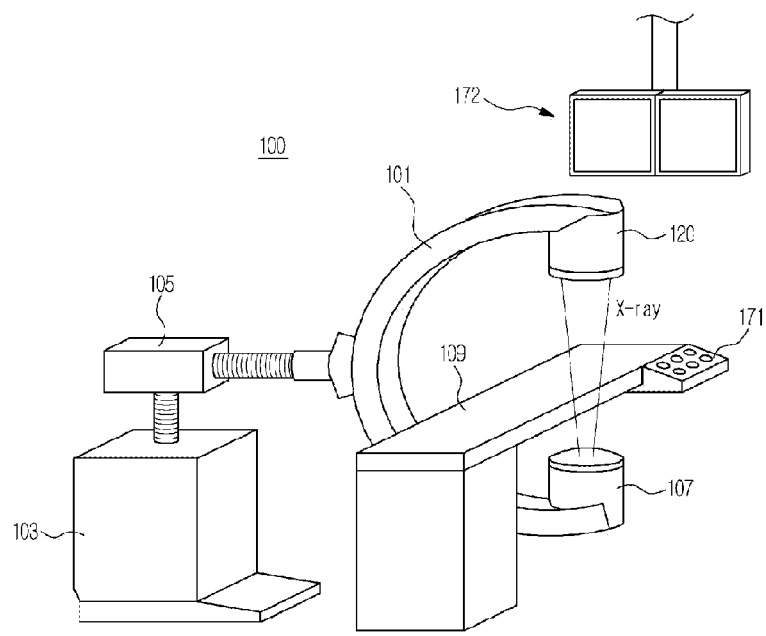
[Fig. 3]
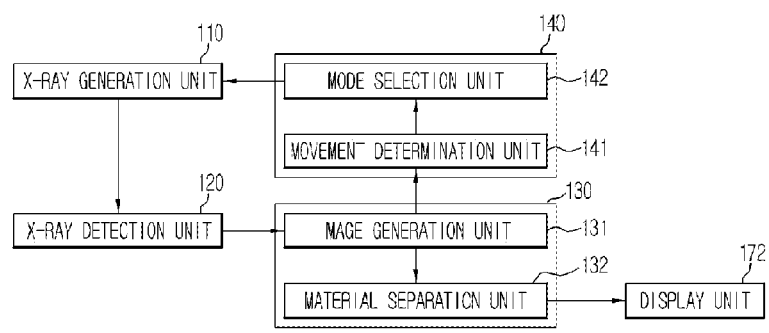

[Fig. 4]
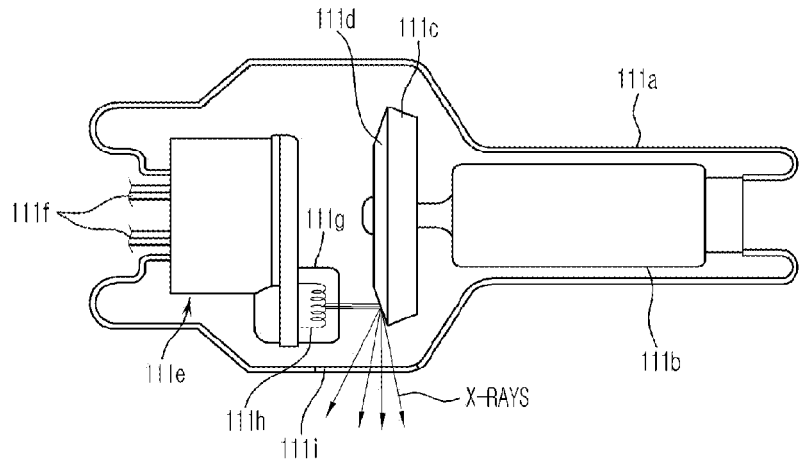
[Fig. 5]
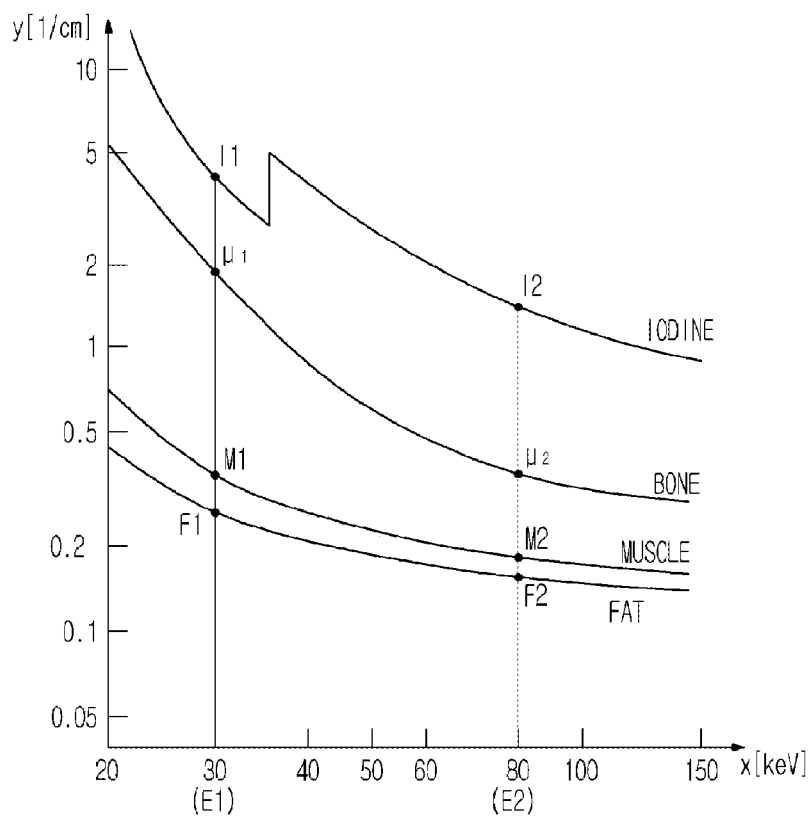
[Fig. 6]
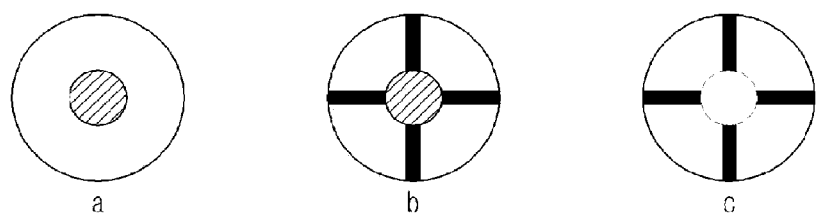

[Fig. 7a]
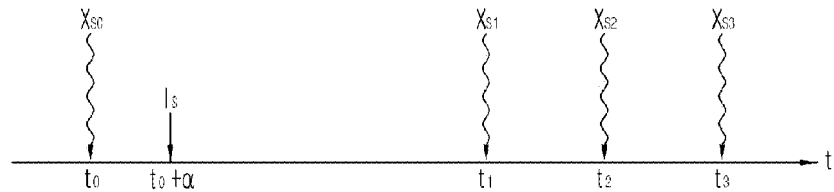
[Fig. 7b]
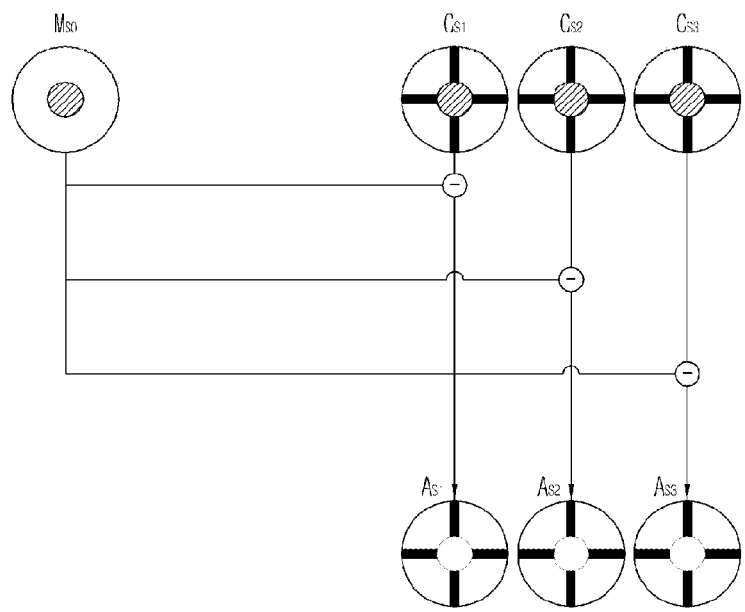
[Fig. 8a]
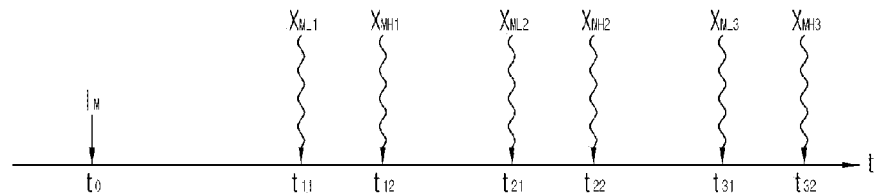

[Fig. 8b]
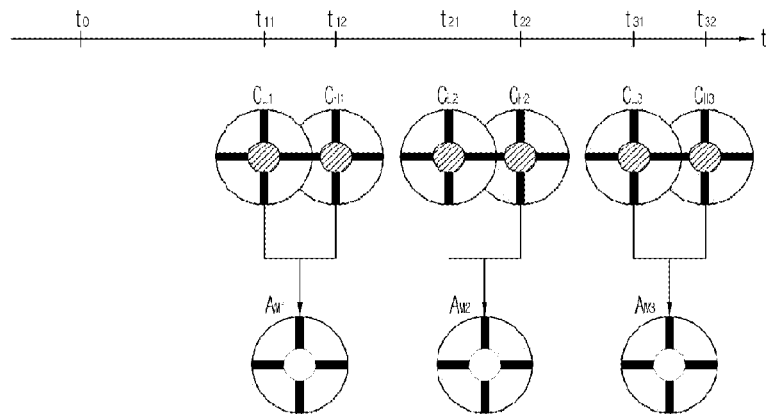
[Fig. 9a]
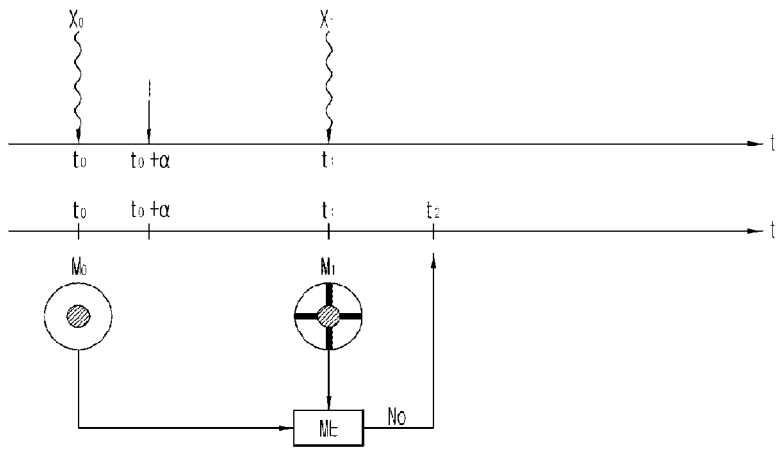
[Fig. 9b]
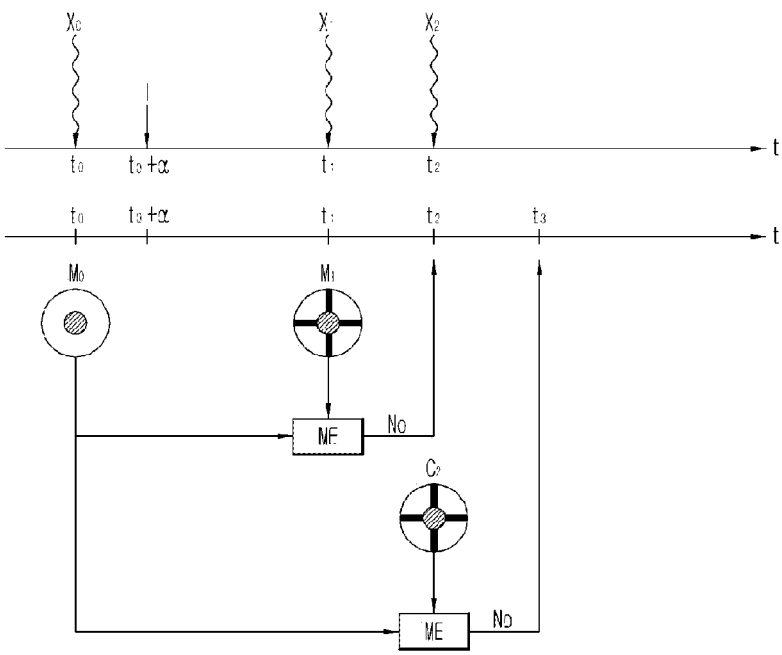

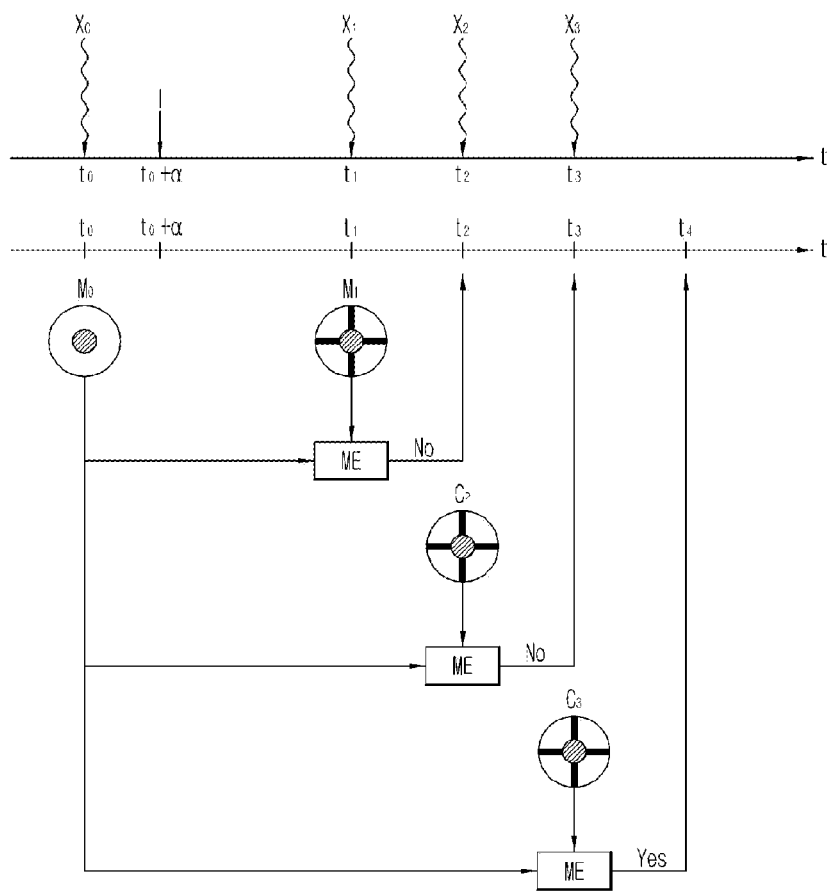
[Fig. 9c]

[Fig. 9d]
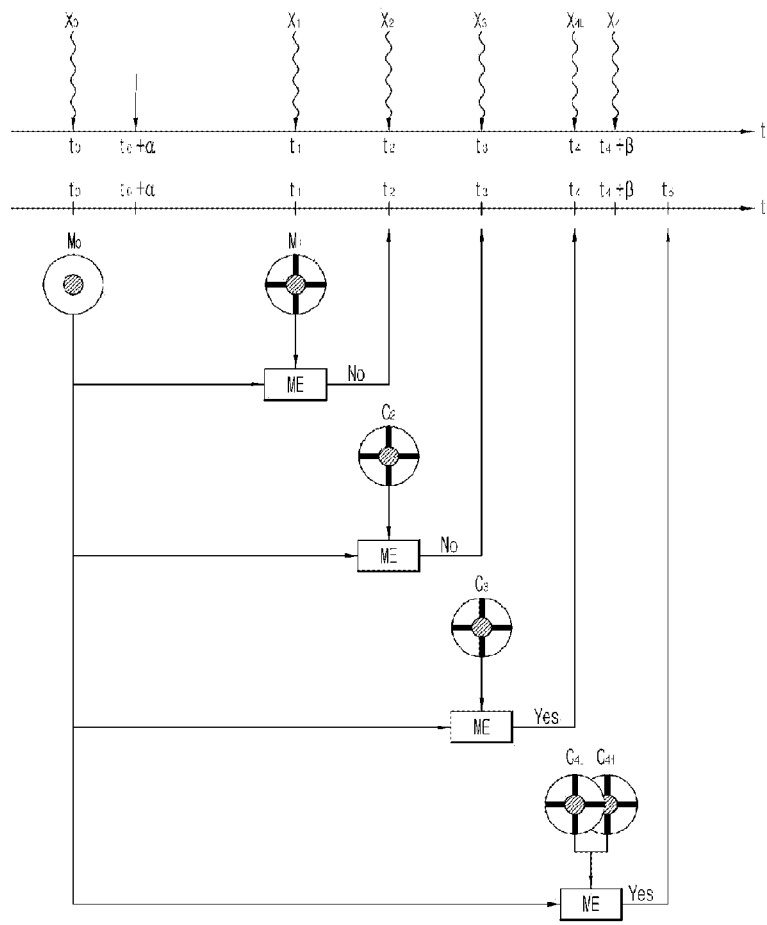
[Fig. 10a]
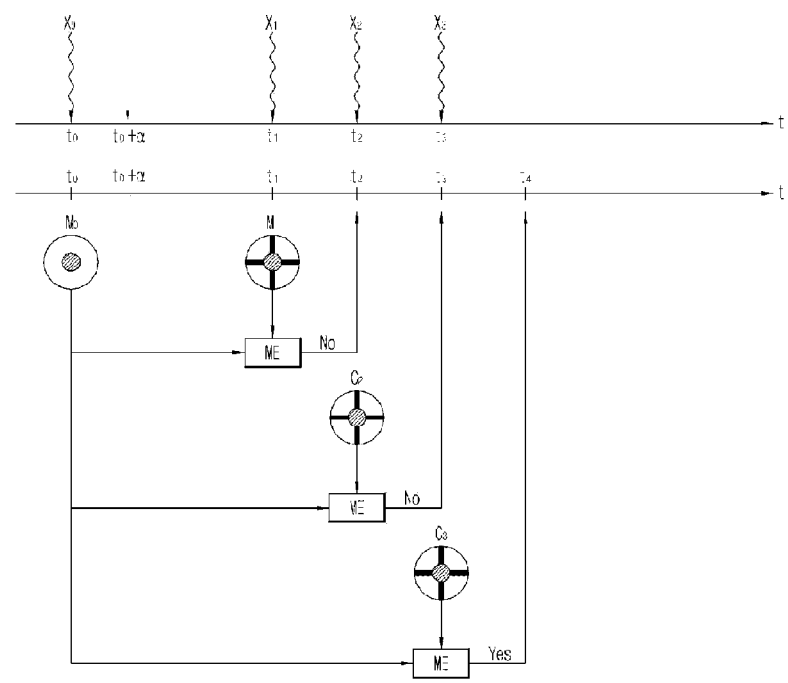

[Fig. 10b]
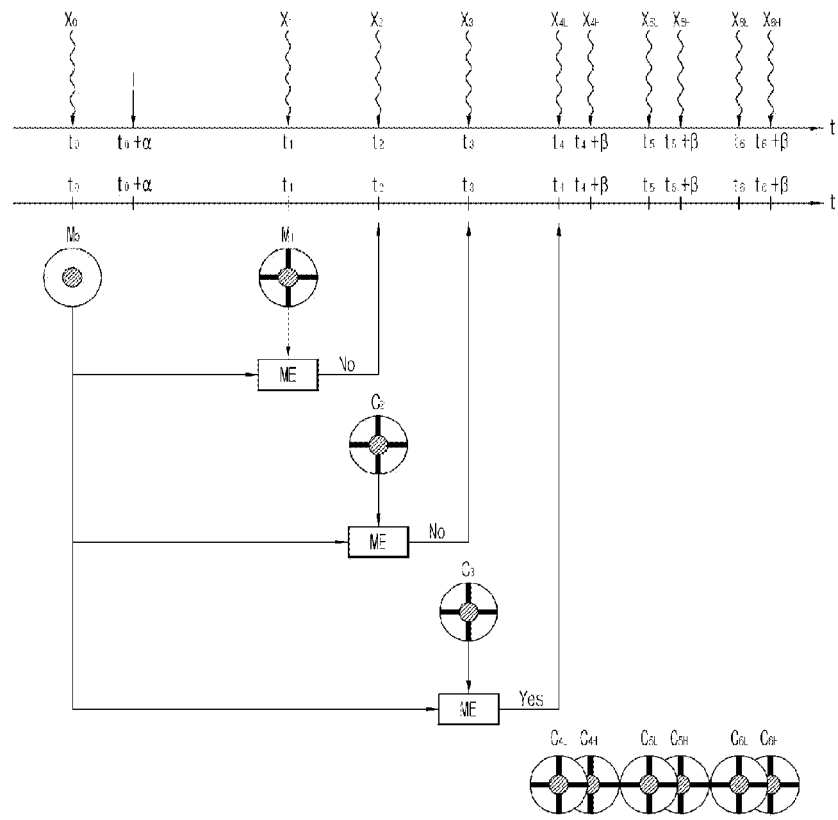
[Fig. 11a]
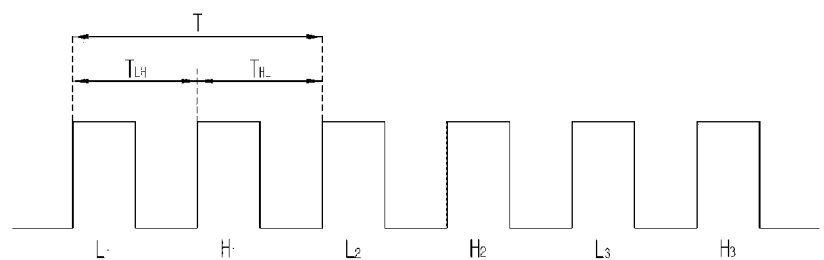
[Fig. 11b]
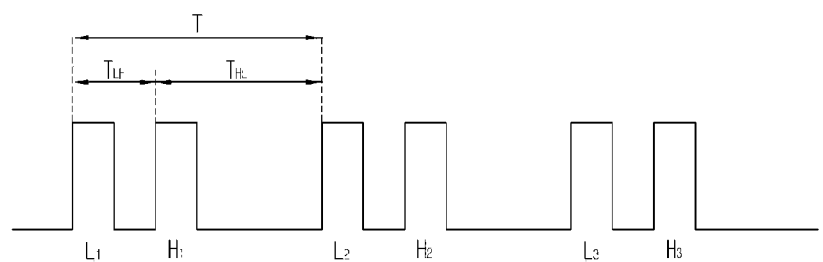

[Fig. 12]
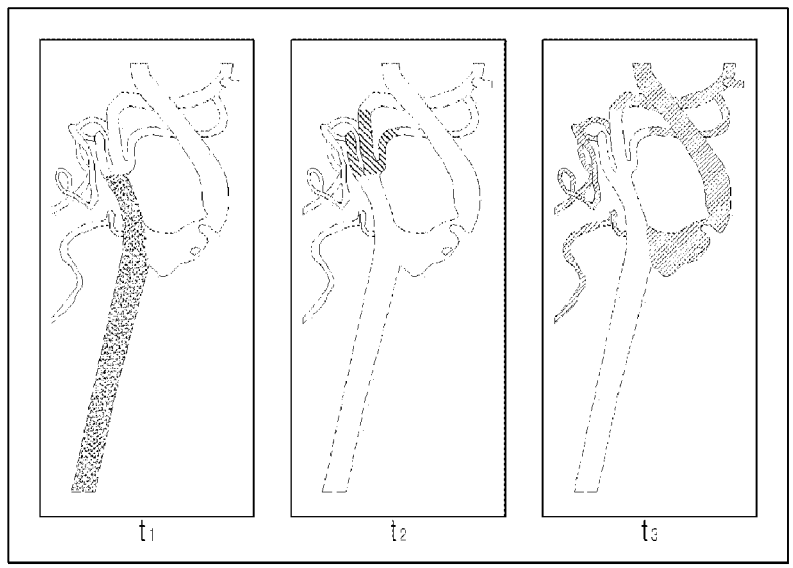
[Fig. 13]
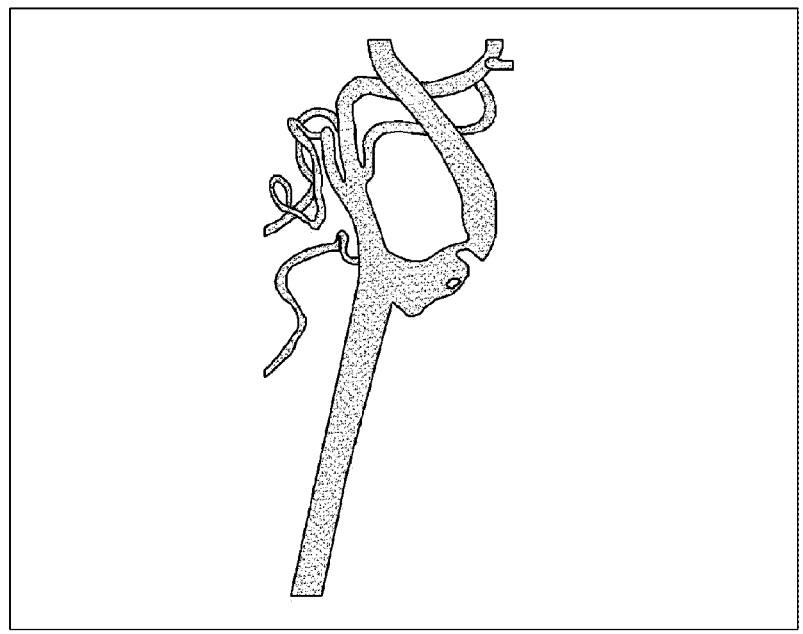

[Fig. 14]
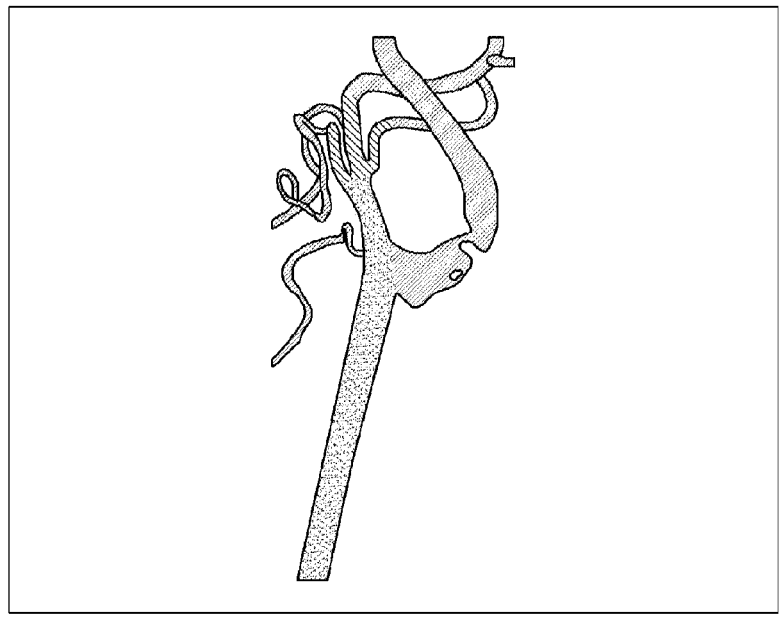
[Fig. 15]
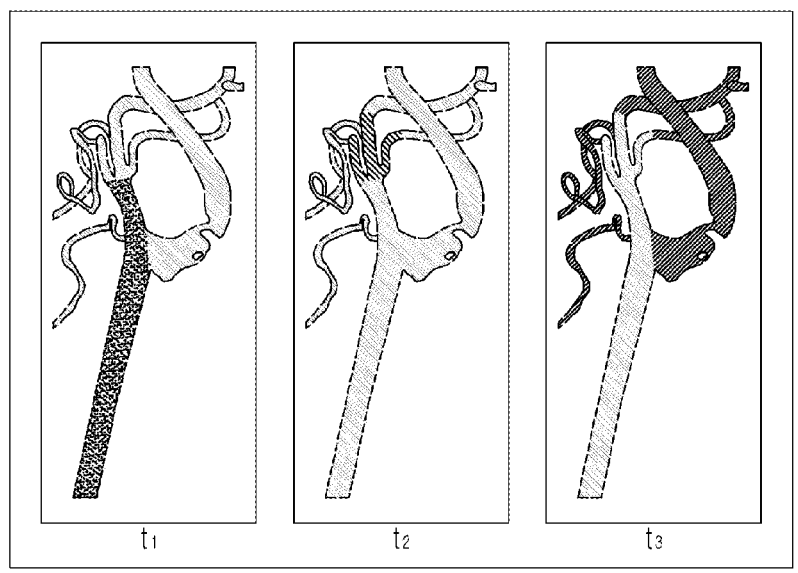

[Fig. 16]
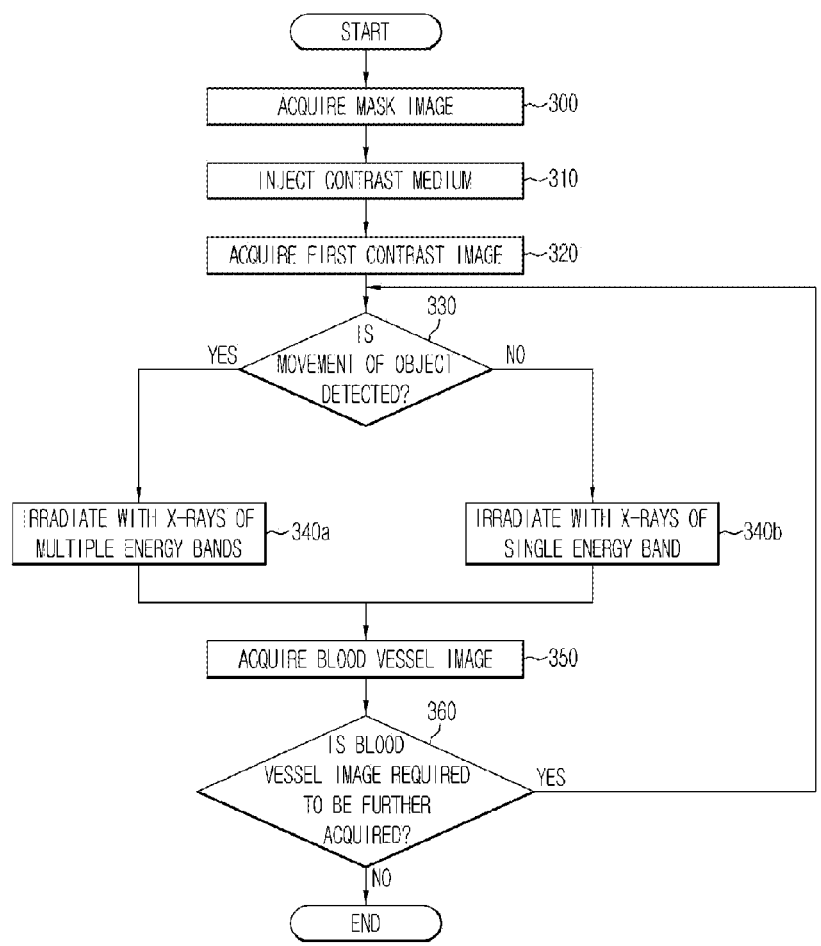

X-RAY IMAGING APPARATUS AND CONTROL METHOD FOR THE SAME

CROSS-REFERENCE TO RELATED APPLICATIONS AND CLAIM OF PRIORITY

The present application claims priority under 35 U.S.C. § 365 to International Patent Application No. PCT/KR2014/009268 filed Oct. 1, 2014, entitled "X-RAY IMAGING APPARATUS AND CONTROL METHOD FOR THE SAME", and, through International Patent Application No. PCT/KR2014/009268, to Korean Patent Application No. 10-2013-0117178 filed Oct. 1, 2013, each of which are incorporated herein by reference into the present disclosure as if fully set forth herein.

TECHNICAL FIELD

Embodiments of the present invention relate to an X-ray imaging apparatus that generates X-ray images by transmitting X-rays through an object and a control method for the same.

BACKGROUND ART

An X-ray imaging apparatus is an apparatus which irradiates an object with X-rays and acquires internal images of the object using the X-rays transmitted through the object. Since permeability of the X-rays is different according to characteristics of a material constituting the object, an internal structure of the object may be imaged by detecting an intensity or strength of the X-rays transmitted through the object.

Specifically, when an X-ray generation unit generates X-rays and irradiates an object with the generated X-rays, an X-ray detection unit detects the X-rays transmitted through the object and converts the detected X-rays into electric signals. Since the conversion to the electric signals is performed for each pixel, a single X-ray image may be obtained by combining electric signals corresponding to each pixel.

As a part of the X-ray image, a digital subtraction angiography image is widely utilized. However, the digital subtraction angiography image has drawbacks in that a motion artifact may occur when the patient moves.

DISCLOSURE OF INVENTION

Technical Problem

Therefore, it is an aspect of the present invention to provide an X-ray imaging apparatus which may determine movements of an object and irradiate the object with X-rays corresponding to the determined movements to determine a radiation pattern, and a control method for the same.

Additional aspects of the invention will be set forth in part in the description which follows and, in part, will be obvious from the description, or may be learned by practice of the invention.

Solution to Problem

In accordance with one aspect of the present invention, a control method for an X-ray imaging apparatus includes: acquiring a mask image by irradiating an object with X-rays; determining a movement of the object based on the mask image; generating a plurality of X-ray images of mutually different energy bands when the movement of the object is detected, and generating a single X-ray image of a single energy band when the movement of the object is not detected; and acquiring a blood vessel X-ray image based on the generated X-ray image.

In accordance with another aspect of the present invention, an X-ray imaging apparatus includes: an X-ray generation unit that irradiates an object with X-rays; an X-ray detection unit that acquires X-ray data by detecting X-rays transmitted through the object; an image processing unit that generates an X-ray image based on the acquired X-ray data, and acquires a blood vessel X-ray image of the object from the X-ray image; and a control unit that determines a movement of the object, generates a plurality of X-ray images of mutually different energy bands to acquire the blood vessel X-ray image when the movement of the object is detected, and generates an X-ray image of a single energy band to acquire the blood vessel X-ray image when the movement of the object is not detected.

Advantageous Effects of Invention

According to the X-ray imaging apparatus and the control method for the X-ray imaging apparatus, the X-ray irradiation pattern may be determined in accordance with the movement of the object, and therefore image quality of the acquired X-ray images may be improved.

BRIEF DESCRIPTION OF DRAWINGS

These and/or other aspects of the invention will become apparent and more readily appreciated from the following description of the embodiments, taken in conjunction with the accompanying drawings of which:

FIG. 1 illustrates an appearance of a general X-ray imaging apparatus;

FIG. 2 illustrates an appearance of an X-ray imaging apparatus for angiography;

FIG. 3 is a control block diagram illustrating an X-ray imaging apparatus in accordance with one embodiment of the present invention;

FIG. 4 illustrates a configuration of an X-ray tube;

FIG. 5 is a graph illustrating a relationship between energy and an attenuation coefficient for each material inside an object;

FIG. 6 is a schematic diagram illustrating an X-ray image used in a subtraction method;

FIG. 7A is a diagram illustrating a method of generating X-rays in accordance with a temporal subtraction method;

FIG. 7B is a diagram illustrating a method of acquiring a blood vessel X-ray image in accordance with a temporal subtraction method;

FIG. 8A is a diagram illustrating a method of generating X-rays in accordance with an energy subtraction method;

FIG. 8B is a diagram illustrating a method of acquiring a blood vessel X-ray image in accordance with an energy subtraction method;

FIGS. 9A, 9B, 9C, and 9D are diagrams illustrating a control unit that controls an X-ray irradiation pattern in accordance with movements of an object in accordance with one embodiment of the present invention;

FIGS. 10A and 10B are diagrams illustrating a control unit that controls an X-ray irradiation pattern in accordance with movements of an object in accordance with another embodiment of the present invention;

FIGS. 11A and 11B are diagrams illustrating an X-ray pulse irradiated from an X-ray generation unit in accordance with an energy subtraction method;

FIG. 12 is a diagram illustrating a method of simultaneously displaying blood vessel X-ray images that are classified in accordance with an acquisition time point, in accordance with one embodiment of the present invention.

FIG. 13 is a diagram illustrating a method of displaying a plurality of blood vessel X-ray images that are overlapped, in accordance with one embodiment of the present invention.

FIG. 14 is a diagram illustrating a blood vessel X-ray image in which a color or a shade of a blood vessel area is differentiated and displayed according to an acquisition time point of the image.

FIG. 15 is a diagram illustrating a method of simultaneously displaying blood vessel X-ray images that are acquired at respective points of time, in accordance with one embodiment of the present invention.

FIG. 16 is a flowchart illustrating a control method of an adaptive X-ray imaging apparatus to a movement of an object in accordance with one embodiment of the present invention.

BEST MODE FOR CARRYING OUT THE INVENTION

Reference will now be made in detail to the embodiments of the present invention, examples of which are illustrated in the accompanying drawings, wherein like reference numerals refer to like elements throughout.

A structure or an imaging method of an X-ray imaging apparatus may vary in accordance with an imaging region, a type of an X-ray image, or an imaging purpose. Specifically, a general X-ray imaging apparatus for imaging a chest, arms, legs, etc., an X-ray imaging apparatus using mammography, an X-ray imaging apparatus using fluoroscopy, an X-ray imaging apparatus using angiography or cardiovascular angiography, an X-ray imaging apparatus using computed tomography, and the like are used, and the X-ray imaging apparatus in accordance with one embodiment of the present invention may be any one of the above-described X-ray imaging apparatuses or a combination of at least two thereof.

The following description will be made under the assumption that x-rays of a single energy band includes monochromatic X-rays and single polychromatic X-rays.

FIG. 1 illustrates an appearance of a general X-ray imaging apparatus.

Referring to FIG. 1, a general X-ray imaging apparatus 100 may include an X-ray generation unit 110, an X-ray detection unit 120, and a host device 170.

The X-ray generation unit 110 may generate X-rays in order to obtain an X-ray image for an object 35 and irradiate a subject 30 with the generated X-rays.

Here, the subject 30 may be a living body of a human being or animal, but the subject in accordance with one embodiment of the present invention is not limited thereto. That is, anything can be the subject as long as its internal structure can be imaged by the X-ray imaging apparatus 100.

In addition, the object 35 means a portion to be diagnosed inside the subject 30 using the X-ray imaging apparatus 100, that is, a radiography part. Thus, as shown in FIG. 1, when the subject 30 is placed on a table, the object 35 may be a head, a chest, arms, legs, or the like.

The X-ray generation unit 110 may be mounted on a ceiling so as to be movable in the longitudinal direction of the table. The X-ray generation unit 110 is moved in the longitudinal direction of the table, whereby a position of the X-ray generation unit 110 may correspond to a position of the object 35.

The X-ray detection unit 120 may be disposed on the opposite side of the X-ray generation unit 110 with the object 35 interposed therebetween, thereby detecting X-rays which are irradiated from the X-ray generation unit 110 and transmitted through the object 35. In addition, the X-ray detection unit 120 may convert the detected X-rays into electric signals.

The X-ray detection unit 120 may be mounted inside the table so as to be movable in the longitudinal direction of the table. In the same manner as in the X-ray generation unit 110, a position of the X-ray detection unit 120 may be moved so as to correspond to the position of the object 35 in the longitudinal direction of the table.

Unlike FIG. 1, the subject 30 may be placed on the table, the X-ray generation unit 110 may be mounted on the ceiling so as to be movable in the longitudinal direction of the table, and the X-ray detection unit 120 may be mounted inside the table so as to be movable in the longitudinal direction of the table.

The host device 170 may include an input unit 171 that receives instructions from a user and a display unit 172 that displays X-ray images, and provide a user interface. Here, the user is a person who performs diagnosis on the object 35 and may be a medical staff such as a doctor, a radiologist, a nurse, and the like, but is not limited thereto. That is, anyone using the X-ray imaging apparatus 100 may be the user.

The input unit 171 may include at least one of a switch, a keyboard, a track ball, and a touch screen, but is not limited thereto.

A cathode ray tube (CRT), a liquid crystal display (LCD), a light emitting diode (LED), or the like may be applied as the display unit 172, but the display unit 172 is not limited thereto.

FIG. 2 illustrates an appearance of an X-ray imaging apparatus for angiography.

The X-ray imaging apparatus 100 may have a C-arm structure as shown in FIG. 2. An X-ray generation assembly 107 and the X-ray detection unit 120 may be respectively mounted in both ends of a C-shaped arm 101 (C-arm). The C-arm 101 may be connected to a main body 103 through a connection shaft 105 to be rotatable in an orbital direction.

The X-ray generation unit 110, a collimator, and a filtering unit are provided inside the X-ray generation assembly 107. A patient table 109 is located between the X-ray generation assembly 107 and the X-ray detection unit 120. When an object is positioned on the patient table 109, the X-ray generation unit 110 irradiates the object with X-rays, and the X-ray detection unit 120 acquires an X-ray image of the object by detecting the irradiated X-rays.

The X-ray imaging apparatus 100 for angiography may perform radiography in accordance with various imaging modes, and obtain real-time moving images for the object, and therefore a user may perform a treatment or diagnosis while viewing the display unit 172 which includes a plurality of screens and displays various images required for the treatment or diagnosis.

The user may input required information through the input unit 171 provided in the X-ray imaging apparatus 100. For example, the user may input a cycle through the input unit so that the X-ray generation unit which will be described later can repeatedly irradiate X-rays. The input cycle may be transmitted to a control unit 140, and the control unit 140 may control the X-ray generation unit 110 in accordance with the input cycle.

FIG. 3 is a control block diagram illustrating an X-ray imaging apparatus 100 in accordance with one embodiment of the present invention.

Referring to FIG. 3, the X-ray imaging apparatus 100 in accordance with one embodiment of the present invention may include the X-ray generation unit 110 that generates X-rays and irradiates the object 35 with the generated X-rays, the X-ray detection unit 120 that acquires X-ray data by detecting the X-rays transmitted through the object 35, and an image processing unit 130 that converts the X-ray data into X-ray images. In addition, the X-ray imaging apparatus 100 accordance with one embodiment of the present invention may further include the control unit 140 that controls an X-ray irradiation pattern of the X-ray generation unit 110.

The X-ray generation unit 110 generates X-rays and irradiates the object 35 with the generated X-rays. The X-ray generation unit 110 generates the X-rays by receiving power from a power supply unit (not shown). Here, energy of the X-rays can be controlled by at least one of a tube voltage and a filter, and a dose or an intensity of the X-rays can be controlled by a tube current or an exposure time of the X-rays.

The X-ray generation unit 110 may irradiate monochromatic X-rays or polychromatic X-rays, but in the present embodiment, the X-ray generation unit 110 irradiates the polychromatic X-rays, and an energy band of the irradiated X-rays is determined by an upper limit and a lower limit.

The X-ray generation unit 110 includes an X-ray tube 111 that generates X-rays.

FIG. 4 illustrates a configuration of an X-ray tube.

Referring to FIG. 4, the X-ray tube 111 may be implemented as a bipolar vacuum tube including an anode 111c and a cathode 111e, and the tube may be a glass tube 111a made of a rigid silicate glass or the like.

The cathode 111e includes a filament 111h and a focusing electrode 111g for focusing electrons, and the focusing electrode 111g may be referred to as a focusing cup. Thermoelectrons are generated in such a manner that the inside of the glass tube 111a is in a high vacuum state of about 10 mmHg and the filament 111h of the cathode is heated at a high temperature. A tungsten filament may be used as one example of the filament 111h, and the filament 111h may be heated by applying a current to an electric conductor 111f connected to the filament. However, the embodiment of the present invention is not limited to an example of employing the filament 111h as the cathode 111e, and a carbon nanotube capable of being driven at a high-speed pulse may be used as the cathode.

The anode 111c is generally made of copper, and a target material 111d is applied or disposed on a side of the anode 111c facing the cathode 111e. Here, as the target material, high-resistance materials such as Cr, Fe, Co, Ni, W, Mo, and the like may be used. As a melting point of the target material becomes higher, a focal spot size is reduced.

When a high voltage is applied between the cathode 111e and the anode 111c, thermoelectrons are accelerated and collide with the target material 111d, thereby generating X-rays. The generated X-rays are irradiated to the outside through a window 111i, and a beryllium (Be) thin film may be used as a material of the window.

The target material 111d may be rotated by a rotor 111b, and when the target material 111d is rotated, a heat accumulation factor may be increased 10 times or more per unit area in comparison with a case in which the target material 111d is fixed, and the focal spot size may be reduced.

The voltage applied between the cathode 111e and the anode 111c of the X-ray tube 111 may be referred to as a tube voltage, and a magnitude of the tube voltage may be displayed as a peak value kvp. When the tube voltage is increased, a speed of the thermoelectrons is increased and thereby the thermoelectrons collide with the target material to generate X-rays. As a result, energy of the generated X-rays (energy of photons) is increased. A current flowing in the X-ray tube 111 is referred to as a tube current, and may be displayed as an average value mA. When the tube current is increased, a dose of the X-rays (the number of photons of the X-rays) is increased.

Thus, an energy band of the X-rays can be controlled by the tube voltage, and an intensity or dose of the X-rays can be controlled by the tube current and an exposure time of the X-rays, and therefore an energy band and intensity of the irradiated X-rays can be controlled in accordance with types or characteristics of the object 35.

The X-ray generation unit 110 generates X-rays using the above-described X-ray tube 111, and irradiates the subject 30, more precisely, the object 35, with the generated X-rays.

When the X-ray generation unit 110 irradiates the object 35 with the X-rays, a degree of attenuation of the X-rays differs in accordance with a material inside the object 35 and the energy band of the irradiated X-rays. Here, a numerical representation of the degree of attenuation of the X-rays is called an attenuation coefficient.

First, the attenuation coefficient may be changed depending on the material inside the object 35.

This is illustrated in FIG. 5. FIG. 5 is a graph illustrating a relationship between energy and an attenuation coefficient for each material inside an object. An X-axis represents energy of photons radiated to the object 35, and a Y-axis represents an attenuation coefficient.

Referring to the graph of FIG. 5, a curved line representing an attenuation coefficient of bones is located above a curved line representing an attenuation coefficient of soft tissue (muscle or fat), and a curved line representing an attenuation coefficient of iodine is located above the curved line representing the attenuation coefficient of bones. Specifically, when X-rays of the same energy band, for example, E1 are irradiated, the attenuation coefficient μ1 of bones is larger than the attenuation coefficient M1 of muscles, the attenuation coefficient M1 of muscles is larger than the attenuation coefficient F1 of fats, and the attenuation coefficient I1 of iodine is larger than the attenuation coefficient μ1 of bones.

That is, mutually different materials inside the object 35 have mutually different attenuation coefficients, and the attenuation coefficient is increased as an atomic number or density of the material becomes higher.

Second, the attenuation coefficient may be changed depending on an energy band of the irradiated X-rays.

In the graph of FIG. 5, when the X-rays having energy bands E1 and E2 are respectively irradiated to bones which are materials inside the object 35, the attenuation coefficient in the lower energy band μ1 is larger than the attenuation coefficient in the higher energy band μ2. Even in a case in which the materials inside the object 35 are muscles or fats, it can be found that the attenuation coefficient M1 or F1 when the X-rays of the lower energy band E1 are irradiated are larger than the attenuation coefficient M2 or F2 when the X-rays of the higher energy band E2 are irradiated. In addition, the same result can be found in the iodine.

That is, as the energy band of the X-rays irradiated to the object 35 becomes lower, the attenuation coefficient may be increased.

Such an attenuation coefficient may be represented as the following Equation 1.

$$I = I_0 \cdot e^{-\mu(E)T} \quad \text{[Equation 1]}$$

Here, I0 denotes an intensity of X-rays irradiated on a material, I denotes an intensity of X-rays transmitted through the material, and μ(E) denotes an attenuation coefficient of the material with respect to X-rays having energy E. T denotes a thickness of the material through which the X-rays are transmitted.

In Equation 1, it can be seen that an intensity of the transmitted X-rays is reduced as the attenuation coefficient is increased (that is, as hardness of the material increases or as the energy band of the X-rays decreases) and a thickness of the material is increased.

In order to obtain X-ray images of dynamic organs such as blood vessels, imaging is required a plurality of times. Thus, in general, a user sets an imaging cycle through the input unit 171, and X-rays are irradiated on the object 35 for each cycle, so that a change in the object over time may be reflected in the X-ray images.

In this instance, in order to obtain blood vessel X-ray images, the X-ray may be irradiated in accordance with a temporal subtraction method or an energy subtraction method. In particular, in an energy subtraction method, an energy band of the irradiated X-rays can be changed. That is, since an attenuation coefficient of iodine that is a component of a contrast medium is changed in accordance with the energy band of the irradiated X-rays, only images of blood vessels can be separated from the X-ray images.

For this, the X-rays of a plurality of energy bands having a fixed cycle may be generated, and sequentially irradiated to the object 35. In order to reduce errors (motion artifacts) due to irradiation time differences among the sequentially irradiated X-rays in this process, the X-rays may be non-uniformly irradiated. This will be described later.

Referring again to FIG. 3, the X-ray detection unit 120 detects the X-rays transmitted through the object 35, and converts the detected X-rays into electric signals to acquire X-ray data.

In general, the X-ray detection unit 120 may be classified according to the method of constituting materials, the method of converting the detected X-rays into the electric signals, the method of acquiring the X-ray data, and various methods through which the X-ray detection unit detects the X-rays and converts the detected X-rays into the electric signals to acquire the X-ray data will be described herein.

First, the X-ray detection unit 120 is classified according to the method by which it converts the X-rays into the electric signals, which may be a direct conversion method or an indirect conversion method.

In the direct conversion method, when the X-rays are irradiated, pairs of electrons and holes are temporarily created inside a light receiving element, and the electrons and the holes are respectively moved to the anode and the cathode by an electric field applied to both ends of the light receiving element. Here, the X-ray detection unit converts such movement into electric signals. In the direct conversion method, as a material of the light receiving element, a-Se, CdZnTe, HgI2, PbI2, or the like may be used.

In the indirect conversion method, a scintillator is provided between the light receiving element and the X-ray generation unit, photon having a wavelength in a visible light region are emitted by reaction between the X-rays irradiated from the X-ray generation unit and the scintillator, and then the light receiving element detects the emitted photon and converts the detected photons into electric signals. As a material of the light receiving element in the indirect conversion method, a-Si or the like may be used, and as the scintillator, a GADOX scintillator in the form of a thin film, a microcolumnar or needle-like CSI (T1), or the like may be used.

In addition, the X-ray detection unit is classified according to a method by which it acquires the X-ray data, which may be a charge integration mode for storing charge for a certain period of time and then acquiring signals from the stored charge or a photon counting mode for counting photons having energy of threshold energy or more whenever signals are generated by a single X-ray photon.

The X-ray detection unit 120 can acquire a plurality of pieces of X-ray data with respect to mutually different energy bands. Here, as a method of acquiring a plurality of image signals, a method in which the X-ray generation unit 110 irradiates each of a plurality of X-rays having mutually different energy bands and the X-ray detection unit 120 detects the irradiated X-rays, and a method in which the X-ray generation unit 110 irradiates X-rays having a certain energy band once and the X-ray detection unit 120 separates the X-rays for each specific energy band may be used. Here, the mutually different energy bands may mean an energy band in which at least one of the upper limit and the lower limit of the energy band is different.

In the X-ray imaging apparatus in accordance with one embodiment of the present invention, the above-described two methods may be applicable. In particular, when the X-ray generation unit 110 irradiates X-rays having a plurality of mutually different energy bands once, X-ray data can be separated and acquired for each energy band using the X-ray detection unit 120 as a photon counting detector. This will be described later.

The X-ray detection unit 120 detects the X-rays transmitted through the object 35, and converts the detected X-rays into electric signals to output the converted signals.

The image processing unit 130 may acquire an X-ray image based on the X-ray data transmitted from the X-ray detection unit 120. In particular, when acquiring a blood vessel X-ray image, the image processing unit 130 may separate a desired internal tissue from the X-ray data to acquire the blood vessel X-ray image.

The image processing unit 130 may include an image generation unit 131 that generates an X-ray image from the transmitted X-ray data, and a material separation unit 132 that separates a desired internal material from the acquired X-ray image. In addition, the image processing unit 130 may further include a reference data providing unit 133 that provides reference data through the image transmitted from the material separation unit 132 again to the material separation unit 132.

Hereinafter, with reference to FIGS. 5 to 7, a temporal subtraction method and an energy subtraction method will be described as an angiography method, and operations of the image processing unit when performing angiography will be described.

FIG. 6 is a schematic diagram illustrating an X-ray image used in a subtraction method. "a" of FIG. 6 indicates a mask image. The mask image indicates an X-ray image acquired from the object 35 before a contrast medium is injected. "b" of FIG. 6 indicates an X-ray image acquired from the object 35 into which the contrast medium is injected. "c" of FIG. 6 indicates a blood vessel X-ray image finally acquired by the temporal subtraction method.

In general, blood vessels are not visible in a simple X-ray image. However, when the contrast medium is injected into the blood vessels and radiography is performed, the shapes of the blood vessels can be confirmed through the radiography. This method is called angiography.

The temporal subtraction method is one angiography technology. FIG. 7 is a diagram illustrating a method of acquiring a blood vessel X-ray image in accordance with the temporal subtraction method. Irradiated X-rays in accordance with the temporal subtraction method have a single polychromatic spectrum.

FIG. 7A is a diagram illustrating a method of generating X-rays in accordance with a temporal subtraction method. XS0, XS1, XS2, and XS3 indicate single energy X-rays whose irradiation time points are respectively t0, t1, t2, and t3. IS indicates a contrast medium injected into the object 35 at a time point of t0+α. FIG. 7B is a diagram illustrating a method of acquiring a blood vessel X-ray image in accordance with a temporal subtraction method. MS0 indicates a mask image acquired at a time point of t0, and CS1, CS2, and CS3 indicate single energy X-ray images acquired at time points of t1, t2, and t3 after the contrast medium is injected. AS1, AS2, and AS3 indicate blood vessel X-ray images acquired in accordance with the temporal subtraction method at time points of t1, t2, and t3 after the contrast medium is injected.

As shown in FIG. 7A, in order to acquire a mask image that is an image before injecting the contrast medium into the object 35, single energy X-rays XS0 are irradiated at a time point of t0. MS0 that is a mask image of FIG. 6B can be acquired from the irradiated X-rays XS0. A contrast medium IS is injected into the object 35 at a time point of t0+α when a predetermined time elapses from the time point of t0. In order to acquire the blood vessel image, single energy X-rays XS1 are irradiated at a desired time point t1 after a sufficient time elapses so that the contrast medium spreads through the blood vessels.

The image generation unit may acquire an X-ray image CS1 from the X-rays XS1 irradiated in this manner after injecting the contrast medium at the time point of t1. The material separation unit receives the X-ray image CS1 acquired after injection of the contrast medium from the image generation unit and compares the received X-ray image CS1 and the mask image MS0. On the assumption that there is no movement of the object, a difference between the two images means distribution of the contrast medium, and therefore it is possible to acquire the blood vessel X-ray image AS1 by obtaining a difference image of the two images at the time point of t1.

According to the temporal subtraction method, there may be a time difference in the image acquisition time between the mask image and the X-ray image. As described above, such a time difference may occur because the X-ray image is acquired after the sufficient time elapses so that the contrast medium spreads within the blood vessels to a prescribed extent. For example, as shown in FIGS. 7A and 7B, there may be a time difference between an acquisition time t0 of the mask image and a subsequent irradiation time t1 of X-rays.

Such a time difference may cause occurrence of an error in the extracted blood vessel X-ray image. Based on the comparison between the X-ray image after the contrast medium is injected and the mask image, when a structural difference of the background and contrast coincide with each other, only the blood vessel area can be accurately extracted. However, when a patient, that is, the subject 30, moves while the contrast medium is spreading, for example, when there is movement caused by breathing of the patient or movement of internal organs caused by cardiac impulse of the patient, geometric deformation of the X-ray image may occur. Alternatively, a unique movement such as contraction or expansion of the object 35 itself may cause occurrence of an error in extraction of the blood vessel area.

In order to reduce such an error, the energy subtraction method may be used. The energy subtraction method is also one angiography technology like the temporal subtraction method. FIG. 8 is a diagram illustrating angiography according to the energy subtraction method. Unlike the temporal subtraction method using the single energy X-rays, X-rays of mutually different energy bands are irradiated to the object 35. In FIG. 8, cases in which low energy X-rays and high energy X-rays are irradiated to the object 35 will be described. Here, a high energy band and a low energy band are relative concepts, and may vary depending on the object 35.

FIG. 8A is a diagram illustrating a method of generating X-rays in accordance with an energy subtraction method. XML1, XML2, and XML3 indicate low energy X-rays whose irradiation time points are t11, t21, and t31, and XMH1, XMH2, and XMH3 indicate high energy X-rays whose irradiation time points are t12, t22, and t32. IM indicates a contrast medium injected into the object 35 at the time point of t0. FIG. 8B is a diagram illustrating a method of acquiring a blood vessel X-ray image in accordance with the energy subtraction method. CL1, CL2, and CL3 indicate low energy X-ray images acquired at time points t11, t21, and t31 after injection of the contrast medium, and CH1, CH2, and CH3 indicate high energy X-ray images acquired at the time points of t12, t22, and t32 after injecting the contrast medium. In addition, AM1, AM2, and AM3 indicate blood vessel X-ray images acquired by the energy subtraction method at the time points t1, t2, and t3 of after injection of the contrast medium.

As shown in FIG. 8A, the contrast medium IM is injected into the object 35 before irradiating the X-rays. In order to obtain the blood vessel image, sufficient time is required after injection of the contrast medium so that the contrast medium spreads through the blood vessels.

First, in order to acquire X-ray images corresponding to two different energy bands, the X-ray generation unit 110 radiates X-rays. For this, the X-ray generation unit 110 radiates X-rays of a high energy band and X-rays of a low energy band. Alternatively, the X-ray generation unit 110 may radiate broadband X-rays including the two energy bands together, and the X-ray detection unit 120 may detect and separate the X-rays into the high energy band and the low energy band. The X-ray detection unit 120 in the X-ray imaging apparatus and the control method for the X-ray imaging apparatus in accordance with one embodiment of the present invention will be described herein under the assumption that X-rays of the high energy band and the low energy band are sequentially radiated. Referring to FIG. 8A, at the time points of t11 and t12 when the sufficient time for the contrast medium to spread has elapsed, low energy X-rays XML1 and high energy X-rays XMH1 are irradiated.

When desiring to separate two kinds of materials from the X-ray image, materials desired to be separated should have different X-ray attenuation characteristics from each other, and X-ray images corresponding to mutually different energy bands should be acquired. For this, the image generation unit 131 may generate X-ray images corresponding to mutually different energy bands. For example, as shown in FIG. 8B, the image generation unit 131 may sequentially generate a low energy X-ray image CL1 and a high energy X-ray image CH1 after injecting the contrast medium so as to correspond to the X-rays XML1 and XMH1.

A brightness difference between the contrast medium (blood vessels; lumens) and body constituents (for example, bones, calcified tissues, and the like) not including the contrast medium which are internal materials to be separated from the X-ray images CL1 and CH1 generated in this manner appears differently. This is because a difference in attenuation characteristics of the internal materials is different for each energy band.

The material separation unit 132 separates a blood vessel image from an original image generated in the image generation unit 131. The material separation unit 132 may separate two material images by performing two operations such as multiplying at least one of the two X-ray images CL1 and CH1 by a weighted value and then performing subtraction. This is called dual-energy X-ray absorptiometry.

For example, in order to separate blood vessels from bones and calcified tissues, a blood vessel image can be acquired by multiplying a low-energy X-ray image CL1 by a certain weighted value and then subtracting the multiplication result from a high-energy X-ray image CH1. That is, images in which bones and calcified materials are removed and blood vessels are clearly visible can be acquired.

As another example, when the number of materials desired to be separated is three or more including blood vessels, the image generation unit 131 may generate at least three X-ray images respectively corresponding to at least three energy bands, and the material separation unit 132 may separate at least three material images including blood vessels by multiplying each image by a proper weighted value and then performing subtraction.

As described above, the X-ray imaging apparatus 100 does not have limitations in the number of materials to be separated, and may acquire an original image in accordance with the number of materials desired to be separated and separate each material image using attenuation characteristics for each material.

In addition, the method of separating the material image by multiplying the image by the weighted value and performing subtraction is merely one method which can be used in the material separation unit 132, and a material separation algorithm for predicting a thickness of each material such as polynomial regression can be used instead of the method of separating the material image.

Unlike FIGS. 8A and 8B, the X-ray generation unit 110 may irradiate an object with X-rays having a plurality of mutually different energy bands for each cycle, and the X-ray detection unit 120 may separate the irradiated X-rays for each energy band and then acquire a plurality of pieces of X-ray data in accordance with the separated X-rays. Since a plurality of X-ray images of mutually different energy bands can be generated through the X-ray data acquired in this manner, blood vessel X-ray images can be acquired using the generated X-ray images in the same manner as in FIGS. 8A and 8Bb. In this case, the X-ray detection unit 120 may be a photon counting detector.

In this manner, the material separation unit 132 may generate a blood vessel X-ray image AM1 using the X-ray images CL1 and CL2. Consequently, by sequentially irradiating with a low-energy X-ray and a high-energy X-ray, a single corresponding blood vessel X-ray image can be acquired.

In the energy subtraction method, a difference (several to several hundred ms) in acquisition time points of the low-energy image and the high-energy image which are the basis for multi-energy based blood vessel X-ray images is smaller than a time difference between a mask image acquisition time point and the X-ray image acquisition time point after injection of the contrast medium in the temporal subtraction method. This is because the time difference between the mask image acquisition time point and the X-ray image acquisition time point after injection of the contrast medium becomes larger over time because a new mask image cannot be acquired while the contrast medium spreads in the temporal subtraction method, but in the energy subtraction method, the mask image is not required and a difference in the acquisition time points between the X-ray images corresponding to mutually different energy bands is constant.

Thus, when the energy subtraction method is applied, a time during which movement of the object 35 occurs is shorter. As a result, the number of errors that can occur by the movement of the object 35 during the difference between the acquisition time points of the two images in the energy subtraction method may be smaller than that in the temporal subtraction method.

However, the blood vessel X-ray image acquired through the energy subtraction method has a lower signal to noise ratio (SNR) than the blood vessel X-ray image acquired through the temporal subtraction method.

According to the thesis (Med. Phys. 16 (6), 1989), when low energy is set as 60 kVp and high energy is set as 120 kVp, an attenuation coefficient of an object corresponding to each energy band can be assumed as $\mu_L^T=22$ cm$^2$/g and $\mu_H^T=6$ cm$^2$/g. Based on this assumption, an SNR with respect to the temporal subtraction method can be obtained as shown in the following Equation 2.

$$SNR_{\Delta T} \propto \frac{\mu_L^T}{\sqrt{(\sigma_L)^2+(\sigma_L)^2}} = 0.71\frac{\mu_L^T}{\sigma_L} \qquad \text{[Equation 2]}$$

Here, $SNR_{\Delta T}$ denotes an SNR with respect to the temporal subtraction method, and $\sigma_L$ denotes a noise level of a low-energy image.

On the other hand, an SNR with respect to the energy subtraction method can be obtained as shown in the following Equation 3.

$$SNR_{\Delta E} \propto \frac{\mu_L^T - R_T\mu_H^T}{\sqrt{(\sigma_L)^2+(R_T)^2(\sigma_H)^2}} = 0.32\frac{\mu_L^T}{\sigma_L} \qquad \text{[Equation 3]}$$

Here $SNR_{\Delta E}$ denotes an SNR with respect to the energy subtraction method, and $R_T$ denotes an attenuation coefficient ratio of an object, which is defined as $R_T=\mu_L^T/\mu_H^T=1.35$. In addition, $\sigma_H/\sigma_L$ denotes a ratio of a noise level of an X-ray image corresponding to each energy band, which satisfies $\sigma_H/\sigma_L=1.3$.

Based on comparison between Equation 2 and Equation 3, it can be found that the energy subtraction method has a lower SNR by approximately 55% than the temporal subtraction method. Since image quality of the image is more clear as the SNR is increased, more clear X-ray images with less noise can be acquired by the temporal subtraction method compared to the energy subtraction method.

As described above, the temporal subtraction method has a high possibility of occurrence of errors due to the movement of the object 35 despite having a higher SNR, whereas the energy subtraction method has a lower SNR than the temporal subtraction method but may reduce the occurrence of errors due to the movement of the object 35.

Thus, in the present invention, by determining the movement of the object 35 in advance and then selecting an appropriate angiography method, it is possible to acquire an X-ray image with more clear image quality.

Referring again to FIG. 3, the control unit 140 may determine the movement of the object 35 in advance and select an X-ray irradiation mode corresponding to the determined movement, and therefore an irraidication pattern including energy or intensity of the X-rays irraidaited to the object 35 from the X-ray generation unit can be controlled.

Specifically, the control unit 140 may include a movement determination unit 141 that determines movement of the object 35, and a mode selection unit 142 that determines an X-ray irradiation pattern of the X-ray generation unit based on the movement determination.

FIGS. 9A, 9B, 9C, and 9D are diagrams illustrating a control unit that controls an X-ray irradiation pattern in accordance with movements of an object in accordance with one embodiment of the present invention.

First, as shown in FIG. 9A, a mask image M can be acquired by irradiating the object 35 with single energy X-rays X0 at a time point of t0. Next, a contrast medium I is injected into the object 35 at a time point of t0+α. Here, the contrast medium I is injected after acquisition of the mask image M, but the contrast medium I may be first injected and then the mask image M may be acquired before the contrast medium I spreads. In this manner, the mask image M may refer to an X-ray image with respect to the object 35 before the contrast medium spreads.

In FIG. 9A, a case in which single energy X-rays are irradiated is illustrated, but a plurality of mask images may be acquired by irradiating the object 35 with multi-energy X-rays.

Next, a first contrast image C1 is acquired by irradiating the object 35 with a single energy X-ray X1 at a time point t1 when the contrast medium sufficiently spreads. After the time point t1, the X-ray is irradiated to the object 35 for each fixed cycle.

In FIG. 9A, the case in which the single energy X-ray are irradiated to the object is illustrated, but a plurality of first contrast images may be acquired by irradiating the object with multi-energy X-rays in the same manner as in acquisition of the mask image.

In this instance, before irradiating the object 35 with the X-rays at a time point t2 included in a second cycle, whether there is movement of the object 35 is determined or predicted. Specifically, the movement determination unit 141 may compare the mask image M and the first contrast image C1 in order to determine whether there is movement of the object 35 in the first cycle or predict whether there will be movement of the object 35 in the second cycle.

The movement determination unit 141 may use a method of evaluating and determining an optical flow or a block-based movement estimation method in order to determine or predict whether there is movement of the object 35 by comparing two images. However, the movement determination unit 141 is not limited to the above-described example, and may use any method that can determine or predict whether there is movement of the object 35.

The movement determination unit 141 may determine whether a difference obtained by comparing two images or a degree of quantified movement is a specific threshold value or larger, thereby determining whether there is movement of the object 35. That is, only when the degree of quantified movement is greater than or equal to a threshold value input by a user or a device internal operation, it may be determined that there is movement of the object 35, and when the degree is less than the threshold value, it may be determined that there is no movement of the object 35.

Alternatively, the movement determination unit 141 may determine a tendency of the difference obtained by comparing the two images or the degree of the quantified movement, thereby determining or predicting whether there is movement of the object 35. As described above, since the X-ray is irradiated to the object 35 for each fixed cycle after the time point t1, the movement of the object 35 may be determined based on images acquired in accordance with the irradiation of the X-ray. Here, when the tendency of the degree of movement is detected to be increased, it is possible to determine that there is movement of the object or predict that there will be movement thereafter.

Unlike this, the movement determination unit 141 may receive a blood vessel X-ray image acquired in accordance with the temporal subtraction method based on the two images, and quantify an energy difference or artifacts of a background to thereby compare the quantified value and the threshold value. Only when the quantified value is greater than or equal to the threshold value, the movement determination unit 141 may determine that there is movement of the object 35 or predict that there will be movement of the object 35 thereafter.

In FIG. 9A, the movement determination unit 141 determines that there is no movement of the object 35 based on the mask image and the first contrast image in the first cycle, and predicts that there will be no movement of the object 35 in the second cycle based on the determination.

The mode selection unit 142 may receive the determination and prediction results from the movement determination unit 141, and control the X-ray generation unit to irradiate the object 35 with single energy X-ray. As shown in FIG. 9B, the X-ray generation unit irradiates the object 35 with the single energy X-ray X2 at a time point t2 included in the second cycle. An X-ray image C2 can be acquired based on the single energy X-ray X2 irradiated at the time point t2.

In the second cycle, the movement determination unit 141 may compare the X-ray image C2, not the first contrast image C1, and the mask image to thereby determine or predict whether there is movement of the object 35. That is, in other cycles except the first cycle, it is possible to determine or predict whether there is movement of the object 35 by comparing the X-ray image acquired in the corresponding cycle and the mask image.

In FIG. 9B, the single energy X-ray image C2 is acquired at the time point t2 included in the second cycle, and the movement determination unit 141 determines that there is no movement of the object 35 by comparing the acquired single X-ray image C2 and the mask image M and predicts that there will be no movement of the object 35 in a third cycle based on the determination result.

Such results are transmitted to the mode selection unit 142, and the mode selection unit 142 controls the X-ray generation unit to irradiate the object with the single energy X-ray. In FIG. 9C, it can be seen that the X-ray generation unit irradiates the object with a single energy X-ray X3 at a time point t3 included in the third cycle.

Based on the single energy X-ray X3 irradiated on the object, a single energy X-ray image C3 may be acquired. Since the corresponding cycle is not the first cycle, the movement determination unit 141 may compare the single energy X-ray image C3 acquired at the time point t3 and the mask image to thereby determine or predict whether there is movement of the object.

In FIG. 9C, the movement determination unit 141 determines that there is movement of the object in the third cycle, and predicts that there will be movement of the object in a fourth cycle. Such results are transmitted to the mode selection unit 142, and the mode selection unit 142 controls an X-ray irradiation pattern of the X-ray generation unit at a time point t4 included in the fourth cycle based on the transmitted results.

Specifically, referring to FIG. 9D, the mode selection unit 142 may control the X-ray generation unit to irradiate the object with dual energy X-rays. The energy subtraction method may reduce an error of an image that occurs by movement compared to the temporal subtraction method, and therefore the mode selection unit 142 may control a plurality of X-rays of mutually different energy bands to be sequentially irradiated to thereby acquire blood vessel X-ray images by the energy subtraction method.

In FIG. 9D, it can be seen that the X-ray generation unit irradiates the object 35 with low energy X-ray X4L at a time point t4 included in the fourth cycle, and irradiates the object 35 with high energy X-ray X4H at a time point t4+β included in the fourth cycle. In FIG. 9D, a case in which dual energy X-rays are sequentially irradiated in accordance with the energy subtraction method is illustrated, but X-rays of mutually different three energy bands or more may be irradiated to the object 35.

In the fourth cycle, a low energy X-ray image C4L may be acquired to correspond to the low energy X-ray X4L, and a high energy X-ray image C4H may be acquired to correspond to the high energy X-ray X4H.

Unlike FIG. 9D, the X-ray generation unit 110 may irradiate the object with X-rays having a plurality of mutually different energy bands in the fourth cycle, and the X-ray detection unit 120 may separate the irradiated X-rays for each energy band and then acquire a plurality of pieces of X-ray data. Through the X-ray data acquired in this manner, a plurality of X-ray images of mutually different energy bands may be generated, and therefore blood vessel X-ray images may be acquired using the generated X-ray images as described in FIG. 9B. In this case, the X-ray detection unit 120 may be a photon counting detector.

In order to determine movement of the object 35 in the fourth cycle or predict the movement of the object in a fifth cycle, C4L or/and C4H and the mask image M may be compared. In FIG. 9D, it can be seen that the movement determination unit 141 determines that there is movement of the object 35 based on the result obtained by determining the movement of the object 35 in the fourth cycle, predicts that there will be movement of the object 35 in the fifth cycle based on the determination result, and transmits the prediction result to the mode selection unit 142.

In this manner, the movement of the object 35 may be determined and an X-ray irradiation pattern may be changed in accordance with the determined movement, and therefore image quality of an X-ray image may be improved by utilizing advantages of each angiography method.

FIGS. 10A and 10B are diagrams illustrating a control unit that controls an X-ray irradiation pattern in accordance with movements of an object in accordance with another embodiment of the present invention.

Referring to FIG. 10A, in order to determine an irradiation pattern of X-rays repeatedly irradiated for each cycle starting from the time point t1, movement of the object 35 is determined. It is determined that there is no movement of the object 35 up to the second cycle, and therefore single energy X-rays X2 and X3 are irradiated to the object 35 at the time points t2 and t3.

In the third cycle, the movement detection unit determines that there is movement of the object 35 based on a result obtained by comparing the single energy X-ray image C3 and the mask image, and predicts that there will be movement of the object 35 in the fourth cycle based on the determination result. The mode selection unit 142 receives the determination or prediction result and controls the X-ray generation unit.

Thus, the X-ray generation unit irradiates the object 35 with dual energy X-rays X4L and X4H at the time point t4 included in the fourth cycle. Based on this, a low energy X-ray image C4L and a high energy X-ray image C4H may be acquired.

In this instance, the movement detection unit may not determine or predict the movement of the object 35 any longer because the movement of the object 35 has been detected in the third cycle.

Presence of the movement of the object 35 at a specific time point may mean that a position of the object 35 at an acquisition time point t0 of the mask image is different from a position of the object 35 at the specific time point, and therefore a position of the object 35 at a time point even after the specific time point is highly likely to be different from the position of the object 35 at the time point t0. Thus, in order to reduce an unnecessary computation amount, on the assumption that there is continually movement of the object 35 after the time point at which the movement of the object 35 is determined, the movement detection unit may not determine or predict the movement of the object 35.

Referring to FIG. 10B, since the movement of the object 35 is detected in the third cycle, the mode selection unit 142 may control the X-ray generation unit to irradiate the object 35 with the dual energy X-rays for each cycle, without determining or predicting the movement any longer after the fourth cycle.

Unlike this, the movement determination unit 141 may set a separate threshold value used for no longer determining the movement. By preventing further determination or prediction of the movement only when the movement greater than or equal to the threshold value is detected, it is possible to no longer determine the movement when it is obviously determined that there is the movement.

In this case, a threshold value that enables the movement to be no longer determined may be larger than a threshold value when it is determined that there is the movement. As a result, the movement determination unit 141 may determine three cases, that is, a case in which there is no movement, a case in which there is movement but the movement is determined again in the following cycle, and a case in which the movement is obviously present and thus not determined any longer.

In addition, unlike FIG. 10B, the X-ray generation unit 110 irradiates the object 35 with X-rays including a plurality of mutually different energy bands for each cycle after the fourth cycle, and the X-ray detection unit 120 separates the irradiated X-rays for each energy band and then acquires a plurality of pieces of X-ray data in accordance with the separated X-rays. Since a plurality of X-ray images of mutually different energy bands may be generated through the X-ray data acquired in this manner, the blood vessel X-ray images may be acquired using the generated X-ray images as described in FIG. 10B. In this case, the X-ray detection unit 120 may be a photon counting detector.

Referring again to FIG. 3, when the mode selection unit 142 selects the energy subtraction method and controls the X-ray generation unit to irradiate with multi-energy X-rays, operations of the X-ray generation unit may be controlled so that the multi-energy X-rays are non-uniformly irradiated during a single cycle. Here, the non-uniformity may mean that an irradiation interval of the irradiated plurality of X-rays is not the same.

FIGS. 11A and 11B are diagrams illustrating an X-ray pulse irradiated from an X-ray generation unit in accordance with an energy subtraction method. Here, it is assumed that multi-energy X-rays have low energy and high energy. In FIG. 11A, an X-ray pulse generated when the multi-energy X-rays are sequentially irradiated in a uniform manner is illustrated, and in FIG. 11B, an X-ray pulse generated when the multi-energy X-rays are sequentially irradiated in a non-uniform manner is illustrated.

When movement of the object 35 is detected while single energy X-rays are irradiated for each fixed cycle in accordance with the temporal subtraction method, the X-rays of a plurality of mutually different energy bands may be sequentially irradiated for each fixed cycle. In this case, multi-energy X-rays may be uniformly irradiated during an input cycle.

For example, as shown in FIG. 11A, when low energy X-ray and high energy X-ray are uniformly and sequentially irradiated in a cycle T, an irradiation interval between low energy X-rays L1 and high energy X-rays H1 which are involved in a single blood vessel X-ray image is TLH, and an irradiation interval between low energy X-rays L2 and high energy X-rays H1 which are involved in mutually different blood vessel X-ray images is THL. In this instance, the multi-energy X-rays are uniformly irradiated, and therefore TLH and THL have the same value.

As described above, there is a time difference TLH between the acquisition time points of the low energy X-ray image and the high energy X-ray image which are the basis when the blood vessel X-ray images are acquired in accordance with the energy subtraction method. Even in such a time interval, movement of the objects 35 and 35 is highly likely to be generated. Thus, by reducing the time difference TLH, a possibility of occurrence of the movement of the objects 35 and 35 may be reduced.

In FIG. 11B, low energy X-rays and high energy X-rays are non-uniformly and sequentially irradiated in a cycle T. Specifically, an irradiation interval between low energy X-rays L1 and high energy X-rays H1 which are involved in a single blood vessel X-ray image is TLH, and an irradiation interval between low energy X-rays L2 and high energy X-rays H1 which are involved in mutually different blood vessel X-ray images is THL. As can be seen in FIG. 9B, since the multi-energy X-rays are non-uniformly irradiated, TLH and THL are different from each other.

In particular, in order to reduce an error due to movement of the object 35 which may occur when acquiring the blood vessel X-ray images in accordance with the energy subtraction method, TLH should be smaller than THL. An irradiation interval THL of X-rays which are involved in mutually different blood vessel X-ray images does not affect the respectively acquired blood vessel X-ray images even if it is significantly long. However, as the irradiation interval of the X-rays which are involved in generation of the single blood vessel X-ray image is shorter, a probability of occurrence of the movement of the objects 35 and 35 may be reduced. Thus, as TLH is smaller, a more accurate blood vessel X-ray image may be acquired.

In FIGS. 11A and 11B, angiography based on X-rays having two kinds of energy, that is, low energy X-rays and high energy X-rays has been described, but energy types of the irradiated X-rays are not limited thereto.

Referring again to FIG. 3, the display unit 172 may display the blood vessel X-ray image acquired in the image processing unit 130 on a screen. A cathode ray tube (CRT), a liquid crystal display (LCD), an organic light emitting diode (OLED), or the like may be applied as the display unit 172, but the display unit 172 is not limited thereto.

The display unit 172 may separate the acquired plurality of blood vessel X-ray images in accordance with the acquisition time points, and display the separated blood vessel X-ray images on a single screen. The display unit 172 may receive the blood vessel X-ray images repeatedly generated for each fixed cycle by the image processing unit 130. The display unit 172 may display the received plurality of blood vessel X-ray images on the single screen, so that a user may grasp a blood flow.

FIG. 12 is a diagram illustrating a method of simultaneously displaying blood vessel X-ray images that are classified in accordance with an acquisition time point, in accordance with one embodiment of the present invention.

The blood vessel X-ray images may be displayed on a single screen in an order in which the blood vessel X-ray images are acquired, and acquisition time points may be displayed together with the blood vessel X-ray images. A portion represented by a dotted line indicates a contour of all of the blood vessels for clarity of understanding, and may not be displayed on the screen. A dark portion is an area in which a contrast medium is present, and shapes of the blood vessels and blood flow information such as a direction of blood flow may be predicted through the dark portion.

It can be seen that a blood flow is located in a low portion of the blood vessel X-ray image acquired at a first time point t1. It can be seen that, in the blood vessel X-ray image acquired at the following time point t2, the blood flow is located above the location of the blood flow confirmed through the blood vessel X-ray image acquired at the time point t1. Thus, it can be found that the blood flow flows upward from a bottom of the screen along the blood vessels. In the blood vessel X-ray image acquired at a final time point t3, it can be seen that the blood flow confirmed through the blood vessel X-ray image acquired at the time point t2 moves in a different direction through the blood vessels.

The display unit 172 may overlap the plurality of blood vessel X-ray images acquired by the image processing unit 130 and display the overlapped image on the screen.

FIG. 13 is a diagram illustrating a method of displaying a plurality of blood vessel X-ray images of FIG. 12 that are overlapped, in accordance with one embodiment of the present invention.

An advancing direction of the blood flow in accordance with the time point and a shape of the blood vessel observed at each time point can be confirmed through FIG. 12, and the plurality of blood vessel X-ray images are overlapped and displayed on a single screen as shown in FIG. 13, thereby enabling a shape of all of the blood vessels to be confirmed. When the shape of all of the blood vessels is confirmed, a user may easily determine whether there is an abnormality in the blood vessels.

FIG. 14 is a diagram illustrating a blood vessel X-ray image in which a color or a shade of a blood vessel area is differentiated and displayed according to an acquisition time point of the image. The plurality of blood vessel X-ray images are overlapped and displayed, and a color or a shade of the plurality of blood vessel X-ray images may be differentiated and displayed as shown in FIG. 14. When the plurality of blood vessel X-ray images are displayed on the screen in this manner, the shape of all of the blood vessels can be confirmed, and the orientation of the blood flow can also be confirmed. When the plurality of blood vessel X-ray images are displayed on the screen in this manner, it can assist in diagnosis of vascular diseases such as arteriosclerosis or cerebral hemorrhaging.

Unlike this, the display unit 172 may display, on the screen, blood flow information internally confirmed by the X-ray imaging apparatus. Based on the overlapped image of FIG. 13, a contour, a length, and a diameter of the blood vessel and blood flow information such as an advancing direction or an advancing speed of the blood flow may be displayed on the screen. Such blood flow information can be confirmed by an internal computation of the X-ray imaging apparatus. Through this, a user can more accurately confirm the blood flow information of the subject 30, and take corresponding action.

Alternatively, unlike the simple overlapped image, a blood vessel X-ray moving image which expresses a blood flow in the actual blood vessel may be displayed on the screen.

First, the material separation unit 132 may convert the plurality of blood vessel X-ray images whose acquisition time points are different from each other into a single blood vessel X-ray moving image. That is, the blood flow information image may include information about the blood flows flowing through the blood vessels between the time point at which the first blood vessel X-ray image is acquired and the time point at which the final blood vessel X-ray image is acquired.

When the blood flow information image is generated, the display unit 172 may display the blood vessel X-ray moving image on the screen. Through this blood flow information image, the blood flow information in accordance with a change in the time point can be visually acquired rather than confirming the blood flow at the specific time point.

In addition, the display unit 172 may differentiate a color of an area in which a blood flow (contrast medium) of the blood vessel X-ray image is positioned and a color of a background area, and display the differentiated colors on the screen.

FIG. 15 is a diagram illustrating a method of simultaneously displaying blood vessel X-ray images that are acquired at respective points of time, in accordance with one embodiment of the present invention.

FIG. 15 is a diagram illustrating a screen in which blood vessel X-ray images acquired at each time point are simultaneously displayed and colors of a background area and a blood flow area are differentiated. Through this, a user can more clearly recognize the shape of the blood vessels, which may become the basis of accurate diagnosis.

In addition to differentiating the colors, the screen may be displayed in such a manner that a weighted value is given to a shade value of an area in which the blood flow is positioned and a shade value of the background area. In the same manner as in the method of differentiating the colors, the display unit 172 may highlight the blood vessels from the background.

FIG. 16 is a flowchart illustrating a control method of an adaptive X-ray imaging apparatus to a movement of an object in accordance with one embodiment of the present invention.

First, in operation 300, a mask image is acquired from an object. The mask image may be a single X-ray image acquired by irradiating the object with single energy X-rays, or a plurality of X-ray images acquired by irradiating the object with multi-energy X-rays. Thus, the mask image may not be limited to the number of irradiated X-rays and any image may be used as the mask image as long as it is imaged before the contrast medium spreads.

In operation 310, the contrast medium is injected into the object after the mask image is acquired. It is difficult to observe a blood flow even though the blood flow is imaged using X-rays, and therefore the contrast medium is injected into the object and movement or a shape of the blood flow may be inferred from a spread path of the injected contrast medium.

In FIG. 16, a case in which the contrast medium is injected into the object 35 after the mask image is acquired has been described, but the contrast medium may be injected into the object 35 and then the mask image may be acquired before the contrast medium spreads. Thus, regardless of the above-described order, it is sufficient that the mask image be acquired before the contrast medium spreads.

In operation 320, a first contrast image is acquired after the contrast medium sufficiently spreads inside the object. Starting from this time point, X-rays are repeatedly irradiated to the object 35 for each fixed cycle. Since the first contrast image is acquired from the object 35 after the contrast medium spreads, the first contrast image has information about blood flows and blood vessels.

In operation 330, whether there is movement of the object is determined or predicted by comparing the acquired first contrast image and the mask image after the first contrast image is acquired. As a method of determining whether there is movement of the object 35, a method of evaluating and determining an optical flow or a block-based movement estimation method may be used.

When the movement of the object 35 is determined or predicted, the blood vessel X-ray image may be acquired in accordance with the energy subtraction method that can reduce an error due to the movement. Thus, in operation S340*a*, a plurality of X-rays of mutually different energy bands are sequentially irradiated to the object in the next cycle of the cycle at which the movement is determined.

Unlike this, the X-ray generation unit 110 may irradiate the object with the X-rays including a plurality of mutually different energy bands in the next cycle of the cycle at which the movement of the object is determined to be present, and the X-ray detection unit 120 may separate the irradiated X-rays for each energy band and then acquire a plurality of pieces of X-ray data in accordance with the separated X-rays. Since a plurality of X-ray images of mutually different energy bands may be generated through the acquired X-ray data, the same result as in the case in which the plurality of X-rays of mutually different energy bands are sequentially irradiated may be obtained. In this case, the X-ray detection unit 120 may be a photon counting detector.

When the movement of the object 35 is not determined or predicted, the blood vessel X-ray image may be acquired in accordance with the temporal subtraction method so that more clear image quality can be obtained than the energy subtraction method. Thus, in operation 340*b*, a single X-ray of a single energy band is irradiated to the object in the next cycle of the cycle at which the movement is determined or the cycle at which the movement is predicted.

In operation 350, a blood vessel X-ray image may be acquired based on the X-ray irradiated in this manner. Specifically, the blood vessel X-ray image may be acquired in accordance with the temporal subtraction method when the single energy X-ray of a single energy band is irradiated, and the blood vessel X-ray image may be acquired in accordance with the energy subtraction method when the plurality of X-rays of mutually different energy bands are irradiated to the object 35.

Since the blood flow may be determined over time through the blood vessel X-ray image, the blood vessel X-ray images are required to be acquired a plurality of times. Thus, in operation 360, whether the blood vessel X-ray image is required to be further acquired is determined. When the blood vessel images are sufficiently acquired, the radiography is completed, and when the blood vessel image is required to be further acquired, the same procedure is repeatedly performed by determining the movement of the object 35.

Although a few embodiments of the present invention have been shown and described, it would be appreciated by those skilled in the art that changes may be made in these embodiments without departing from the principles and spirit of the invention, the scope of which is defined in the claims and their equivalents.

Although the above description has been made under the assumption that the X-ray imaging apparatus senses a movement of an object by using an X-ray image of the object, the control unit of the X-ray imaging apparatus may include a sensor to sense a movement of an object. In this case, the sensor may include an electromagnetic sensor and an optical sensor, and also an electrocardiogram (ECG) sensor to sense of ECG of an object.

The invention claimed is:

1. A control method for an X-ray imaging apparatus comprising:
   determining a movement of an object based on a mask image of the object;
   generating a plurality of X-ray images of mutually different energy bands when the movement of the object is detected, and generating a single X-ray image of a single energy band when the movement of the object is not detected; and
   acquiring a blood vessel X-ray image based on the generated X-ray images.

2. The control method according to claim 1, wherein acquiring the blood vessel X-ray image comprises:
   separating the blood vessel X-ray image from the plurality of X-ray images of mutually different energy bands once a movement of an object is detected; and
   acquiring the blood vessel X-ray image by subtracting the single X-ray image of the single energy band from the mask image once a movement of an object is not detected.

3. The control method according to claim 1, wherein:
   determining the movement of the object includes repeatedly determining the movement of the object for each fixed cycle, and
   acquiring the blood vessel X-ray image includes acquiring the blood vessel X-ray image for each fixed cycle based on the determination.

4. The control method according to claim 3, wherein determining the movement of the object in a first cycle includes:
   acquiring a first contrast image by irradiating the object with X-rays in the first cycle; and
   comparing the first contrast image and the mask image.

5. The control method according to claim 4, wherein the first contrast image includes at least one of the plurality of X-ray images of the mutually different energy bands and the single X-ray image of the single energy band.

6. The control method according to claim 3, wherein determining the movement of the object in a cycle different from a first cycle includes comparing the X-ray image acquired in the cycle and the mask image.

7. The control method according to claim 1, wherein acquiring the mask image includes acquiring at least one of a plurality of mask images of the mutually different energy bands and a single mask image of the single energy band.

8. The control method according to claim 3, wherein determining the movement of the object includes no longer determining the movement of the object once the movement of the object is detected.

9. The control method according to claim 8, wherein generating the X-ray image includes generating the plurality of X-ray images of the mutually different energy bands for each fixed cycle when the movement of the object is detected.

10. The control method according to claim 3, further comprising converting a plurality of blood vessel X-ray images acquired for each fixed cycle into a single blood vessel X-ray moving image.

11. An X-ray imaging apparatus comprising:
    an X-ray generation unit configured to irradiate an object with X-rays;
    an X-ray detection unit configured to acquire X-ray data by detecting X-rays transmitted through the object;
    an image processing unit configured to:
       generate an X-ray image based on the acquired X-ray data, and
       acquire a blood vessel X-ray image of the object from the X-ray image; and
    a control unit configured to:
       determine a movement of the object,
       generate a plurality of X-ray images of mutually different energy bands to acquire the blood vessel X-ray image when the movement of the object is detected, and
       generate an X-ray image of a single energy band to acquire the blood vessel X-ray image when the movement of the object is not detected.

12. The X-ray imaging apparatus according to claim 11, wherein the control unit is configured to:
    control the image processing unit to separate the blood vessel X-ray image from the plurality of X-ray images of mutually different energy bands once a movement of an object is detected; and
    control the image processing unit to acquire the blood vessel X-ray image by subtracting the single X-ray image of the single energy band from a mask image once a movement of an object is not detected.

13. The X-ray imaging apparatus according to claim 11, wherein the control unit is further configured to control the blood vessel X-ray image to be acquired for each fixed cycle by repeatedly determining the movement of the object for the each fixed cycle.

14. The X-ray imaging apparatus according to claim 13, wherein, when determining the movement of the object in a first cycle, the control unit is further configured to compare a first contrast image acquired by controlling the X-ray generation unit to irradiate the object with X-rays in the first cycle and a mask image acquired before the first cycle.

15. The X-ray imaging apparatus according to claim 13, wherein, when determining the movement of the object in a cycle different from a first cycle, the control unit is further configured to compare the X-ray image acquired in the cycle and a mask image acquired before the first cycle.

16. The X-ray imaging apparatus according to claim 13, wherein, when the movement of the object is detected, the control unit is further configured to no longer determine the movement of the object.

17. The X-ray imaging apparatus according to claim 16, wherein, when the movement of the object is detected, the control unit is further configured to generate the plurality of X-ray images of the mutually different energy bands for each fixed cycle to acquire the blood vessel X-ray image.

18. The X-ray imaging apparatus according to claim 13, wherein the image processing unit is further configured to convert a plurality of blood vessel X-ray images acquired for each fixed cycle into a single blood vessel X-ray moving image.

19. The X-ray imaging apparatus according to claim 11, wherein the X-ray generation unit is further configured to change an energy band of the irradiated X-rays by changing at least one of a tube voltage and a filter.

20. The X-ray imaging apparatus according to claim 11, wherein, when the movement of the object is detected, the control unit is further configured to control the X-ray generation unit to sequentially irradiate the object with a plurality of X-rays of the mutually different energy bands.

21. The X-ray imaging apparatus according to claim 11, wherein, when the movement of the object is detected, the control unit is configured to:
    control the X-ray generation unit to irradiate the object with X-rays including the plurality of mutually different energy bands, and
    control the X-ray detection unit to detect the irradiated X-rays and separate the detected X-rays for each of the plurality of energy bands to acquire a plurality of pieces of X-ray data corresponding to each energy band.

22. The X-ray imaging apparatus according to claim 11, wherein the control unit includes a sensor to sense a movement of the object.

* * * * *